United States Patent [19]

Houlachi et al.

[11] Patent Number: 5,411,648
[45] Date of Patent: May 2, 1995

[54] METHOD AND APPARATUS FOR ON-LINE MONITORING THE QUALITY OF A PURIFIED METAL SULPHATE SOLUTION

[75] Inventors: George Houlachi, Ste-Anne-de-Bellevue; M. Barakat I. Janjua, Pointe-Claire; Frank Kitzinger, Montreal; Gregory A. Wint, Pierrefonds; Vladimir M. Labuc, Hudson, all of Canada

[73] Assignee: Noranda Inc., Toronto, Canada

[21] Appl. No.: 181,503

[22] Filed: Jan. 14, 1994

[30] Foreign Application Priority Data

Jan. 21, 1993 [CA] Canada ................................. 2087801

[51] Int. Cl.$^6$ ............................................. G01N 27/26
[52] U.S. Cl. ............................ 204/153.19; 204/153.1
[58] Field of Search ................ 204/153.19, 153.1, 402, 204/412, 434

[56] References Cited

U.S. PATENT DOCUMENTS

| | | | |
|---|---|---|---|
| 3,680,841 | 8/1972 | Yagi et al. ................................. | 259/1 |
| 4,013,412 | 3/1977 | Mukae .................................... | 23/230 |
| 4,146,437 | 3/1979 | O'Keefe ............................ | 204/153.1 |
| 4,229,264 | 10/1980 | Graunke .................................. | 204/1 |
| 4,443,301 | 4/1984 | Kerby .................................... | 204/1 |
| 4,566,949 | 1/1986 | Berger ................................... | 204/402 |
| 4,595,462 | 6/1986 | Vangaever et al. ................. | 204/402 |
| 4,693,790 | 9/1987 | Warren et al. .......................... | 204/1 |
| 4,786,373 | 11/1988 | Saloheimo et al. ..................... | 204/1 |
| 5,298,129 | 3/1994 | Eliash .............................. | 204/153.1 |
| 5,298,130 | 3/1994 | Ludwig ............................ | 204/153.1 |

FOREIGN PATENT DOCUMENTS

| | | |
|---|---|---|
| 0242530 | 10/1987 | European Pat. Off. . |
| 2117120 | 10/1983 | United Kingdom . |
| 88/09400 | 12/1988 | WIPO . |

OTHER PUBLICATIONS

Tabachnikov, *Journal of Analytical Chemistry of the USSR*, 1976, 31 (10), 1361-1364 no month available.

Ashkinazi, *Journal of Analytical Chemistry of the USSR*, 1983, 38 (11), 1514-1518 no month available.

A. W. Bryson, "*A solution quality analyser for zinc sulphate electrolyte*", National Institute for Metallurgy, Johannesburgh, S.A., Report T6C1 no month and year presently available.

Saunders et al. "*An automated instrument for the determination of the effect of impurities on the cathodic current efficiency during the electrowinning of zinc*", National Institute for Metallurgy, Johannesburgh, S.A., Report T6C4 no month and year presently available.

Saunders et al. "*An apparatus for the automatic measurement of current efficiencies during electrodeposition of of nickel in chloride media*", National Institute for Metaullurgy, Johannesburgh, S.A. Report 1778 no month and year presently available.

Tench et al, Cyclic Pulse Voltammetric Stripping Analysis of Acid Copper Plating Baths, Apr. 1985, pp. 831-834.

*Primary Examiner*—John Niebling
*Assistant Examiner*—Bruce F. Bell
*Attorney, Agent, or Firm*—Keck, Mahin & Cate

[57] ABSTRACT

A method and an apparatus for on-line monitoring the quality of a purified metal sulphate solution is disclosed. The method comprises the steps of depositing metal from the purified metal sulphate solution onto a working electrode submerged in the solution by passing constant current through the solution at a current density in the range of 25 to 150 mA/cm$^2$ for a predetermined time interval, dissolving the metal deposited on the working electrode by reversing the polarity of the potential applied between the working electrode and a counter electrode so as to pass a reverse current of the same current density through the solution until all zinc is removed from the working electrode as sensed by a sudden change in electrode potential, deriving the quality index of the solution by calculating the ratio of the dissolution time over the deposition time, and restoring the surface of the counter electrode by effecting the dissolution of the metal deposited on the counter electrode at the end of each measurement.

9 Claims, 1 Drawing Sheet

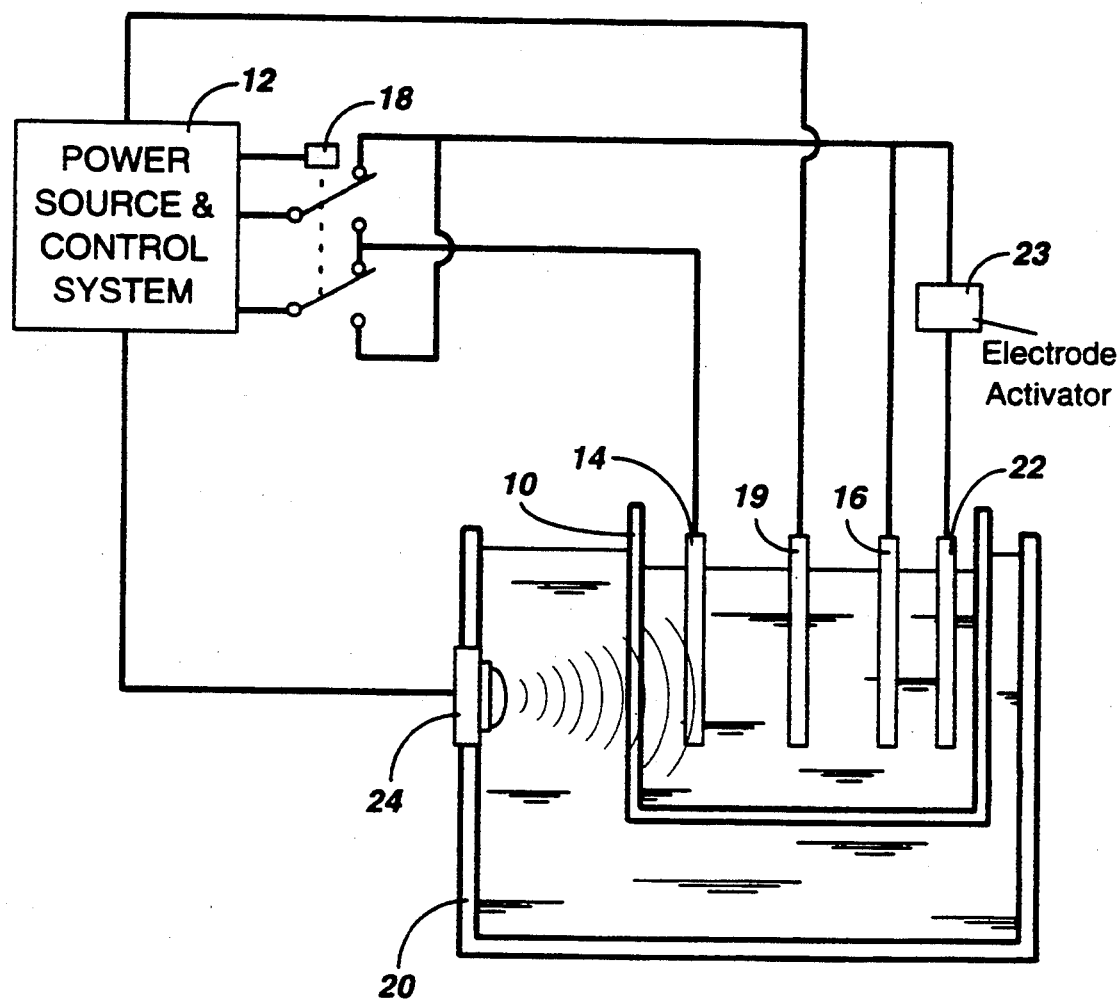

METHOD AND APPARATUS FOR ON-LINE MONITORING THE QUALITY OF A PURIFIED METAL SULPHATE SOLUTION

This invention relates to on-line monitoring the quality of a purified metal sulphate solution, more particularly the quality of a purified zinc sulphate solution used for the electrolytic production of zinc.

A complex multi-stage purification is used in the zinc industry to ensure that the concentration of all detrimental impurities, specifically cobalt, antimony, iron, cadmium and copper, are maintained below certain limits. Fluctuations, however, occur. Analytical methods may be used to monitor the impurity levels but the contributions due to synergistic effects and organic additives would be excluded. The use of quality meters based on the principle of Faraday's law of electromechanical equivalence has also been reported in the literature as illustrated in the following articles: A. P. Saunders, I. Philip and J. P. Martin, "An automated instrument for the determination of the effects of impurities on the cathodic current efficiency during the electrowinning of Zinc", Report No. T6C4, Natn. Inst. for Metallurgy, Johannesburg; A. W. Bryson, "A solution quality analyser for zinc sulphate electrolyte", Report No. T6C1, Natn. Inst. for Metallurgy, Johannesburg.

However, these sensors are not well suited for online monitoring of the quality of the zinc sulphate solution because they are not equipped with means for restoring the surface of the electrodes at the end of each measurement.

SUMMARY OF THE INVENTION

It is the object of the present invention to provide a method and an apparatus which allow complete dissolution of zinc deposited at the end of each measurement so as to provide a clean electrode surface which is required for accurately sensing the effect of detrimental impurities during subsequent measurements.

The method in accordance with the present invention comprises the steps of depositing metal from a purified metal sulphate solution onto a working electrode submerged into the solution by passing constant current through the solution at a current density in the range of 25 to 150 $mA/cm^2$ for a predetermined time interval, dissolving the metal deposited on the working electrode by reversing the polarity of the potential applied between the working electrode and a counter electrode so as to pass a reverse current of the same current density through the solution until all the metal deposited on the working electrode is removed as sensed by a sudden change in electrode potential, and restoring the surface of the counter electrode by effecting the dissolution of all the metal deposited on the counter electrode at the end of each measurement.

Dissolution of the metal deposited on the counter electrode is preferably done galvanically although it could be done electrochemically or chemically.

The metal sulphate solution is preferably a zinc sulphate solution used for the electrolytic production of zinc.

Ultrasonic energy is preferably applied to the electrodes for cleaning the electrodes from loosely adhering material after some use and for ensuring homogeneous composition of the solution.

Sensing of the electrode potential at the end of the dissolution time may be done by means of a suitable voltage level detector connected between the electrodes, or by means of a reference electrode submerged into the solution while being electrically connected to the counter electrode.

The apparatus in accordance with the present invention comprises a cell containing a purified metal sulphate solution, a working electrode and a counter electrode submerged into the solution, means for applying a potential between the working and counter electrodes such as to pass a constant current at a current density in the range of 25 to 150 $mA/cm^2$ through the solution to deposit metal from the purified metal sulphate solution onto the working electrode for a predetermined time interval, means for reversing the potential applied between the working and counter electrodes so as to pass a reverse current of the same current density through the solution until all the metal is removed from the working electrode as sensed by a sudden change in electrode potential, the quality index being derived from the ratio of the dissolution time over the deposition time, and means for introducing a third electrode into the solution at the end of the test to remove any metal deposited on the counter electrode at the end of each measurement so as to leave the counter electrode chemically clean and ready for the next test.

The electrodes are preferably made of graphite. Other electrically stable materials such as Al, Pb—Ag (7%), platinized titanium or conductive ceramics, may also be used.

The third electrode is made of a low hydrogen overvoltage material, specifically noble metal, e.g. platinum or a valve metal covered with a noble metal e.g. platinized titanium. This feature differentiates the instrument of the present invention from prior instruments that were based upon Faraday's law of electrochemical equivalence. Zinc deposited on the counter electrode during the dissolution from the working electrode at the end of the test would not be systematically removed without running into other complications. Combined with the proper choice of electrode material, the galvanic removal of zinc, apart from being many times faster than the anodic removal, leaves the counter electrode chemically clean and ready for the next test.

BRIEF DESCRIPTION OF THE DRAWING

The invention will now be disclosed, by way of example, with reference to the accompanying drawing which illustrates a schematic diagram of the quality meter in accordance with the invention.

DETAILED DESCRIPTION OF THE INVENTION

Referring to the drawing, a sample of zinc sulphate solution is placed in an electrolytic cell 10. Generally speaking, a constant current is passed through the sample solution, first in one direction and then the other. The ratio of the times of the two current flow directions is used to calculate the quality index of the sample solution.

The constant current is provided by a power source and control system 12. Such constant current is passed through the sample solution via working electrode 14 and counter electrode 16. Current is passed through the cell for a predetermined time period of, for example, 100 sec and during that time zinc is deposited on the working electrode 14. The current is then reversed by a polarity reversing relay 18 operated by the power source and control system 12. The time taken to dissolve the zinc deposited on the working electrode is sensed by means of a suitable voltage level sensor connected between the electrodes, or by means of a reference electrode 19 submerged into the solution.

The quality index is calculated as the ratio of the current time periods in the two directions. If the time in one direction (deposition) is 100 sec, then the quality index percentage is numerically equal to the time in seconds for the reverse (dissolution) direction.

During the test, the temperature of the cell is preferably maintained at about 60° C. by placing the cell in a water bath 20 which is thermostatically controlled. Other means of controlling the temperature of the sample may also be used.

Once the test is terminated, the electrodes are cleaned to remove any metal deposited on them in preparation for the following test since as, mentioned previously, the apparatus in accordance with the present invention, is designed for on-line operation. In accordance with the present invention, a low hydrogen-overvoltage metal electrode 22, such as platinized titanium, is submerged into the solution by means of any suitable actuator 23 to galvanically remove any zinc remaining on the counter electrode. When a water bath is used to maintain the temperature of the sample, an ultrasonic transmitter 24 operated by the power source and control system 12 may be used to help cleaning the electrodes. In such a case the electrolytic cell must be made of a material transparent to ultrasonic waves.

We claim:

1. A method for on-line monitoring the quality of a purified metal sulphate solution, comprising the steps of:
   a) depositing metal from the purified metal sulphate solution onto a working electrode submerged in the solution by passing constant current through the solution at a current density in the range of 25 to 150 mA/cm$^2$ for a set time interval;
   b) transferring the metal deposited on the working electrode to a counter electrode by reversing the polarity of the potential applied between the working electrode and the counter electrode to pass a reverse current of the same current density as in step a) through the solution until all zinc is removed from the working electrode as sensed by a sudden change in electrode potential;
   c) calculating the ratio of the dissolution time over the deposition time to obtain a quality index of the solution; and
   d) restoring the surface of the counter electrode by galvanically effecting the dissolution of the metal deposited on the counter electrode at the end of each measurement.

2. A method as defined in claim 1, wherein the metal sulphate solution is a zinc sulphate solution used for the electrolytic production of zinc.

3. A method as defined in claim 1, wherein the electrodes are made of graphite or other electrochemically stable materials.

4. A method as defined in claim 1, wherein ultrasonic energy is applied to the electrodes for cleaning the surface from loosely adhering material and for ensuring homogeneous composition of the solution.

5. A method as defined in claim 1, wherein sensing of the electrode potential is done by measuring the potential across the electrodes or by using a reference electrode submerged into the solution.

6. An apparatus for on-line monitoring the quality of a purified metal sulphate solution comprising:
   a) a cell containing a purified metal sulphate solution;
   b) a working electrode and a counter electrode submerged into the solution;
   c) means for applying a potential between the working and counter electrodes to pass a constant current at a current density in the range of 25 to 150 mA/cm$^2$ through the solution to deposit metal from the purified metal sulphate solution onto the working electrode for a set time interval;
   d) means for reversing the polarity of the constant current applied between the working and counter electrodes to pass a reverse current of the same density through the solution until all the metal is removed from the working electrode as sensed by a sudden change in electrode potential, the quality index is derived from the ratio of the dissolution time over the deposition time; and
   e) means for introducing a third electrode into the solution at the end of the test to remove galvanically any metal deposited on the counter electrode at the end of each measurement to leave the counter electrode chemically clean and ready for the next test.

7. An apparatus as defined in claim 6, wherein the electrodes are made of graphite or other electrochemically stable materials.

8. An apparatus as defined in claim 6, wherein the cell is located in a water bath which is maintained at a temperature of about 60° C.

9. An apparatus as defined in claim 6, wherein the cell is made of a material transparent to ultrasonic waves and further comprising an ultrasonic transmitter submerged in the water bath for applying ultrasonic energy to the electrodes in the cell to clean the electrodes.

* * * * *